United States Patent
Reuss et al.

(10) Patent No.: US 6,406,426 B1
(45) Date of Patent: Jun. 18, 2002

(54) MEDICAL MONITORING AND ALERT SYSTEM FOR USE WITH THERAPEUTIC DEVICES

(75) Inventors: James L. Reuss, Waukesha; Michael J. Henry, Delafield, both of WI (US)

(73) Assignee: Criticare Systems, Waukesha, WI (US)

( * ) Notice: Subject to any disclaimer, the term of this patent is extended or adjusted under 35 U.S.C. 154(b) by 0 days.

(21) Appl. No.: 09/432,530

(22) Filed: Nov. 3, 1999

(51) Int. Cl.[7] .................................................. A61B 5/00
(52) U.S. Cl. ........................ 600/300; 128/920; 128/903; 128/104
(58) Field of Search ................................ 600/300–301; 705/2–3, 9; 128/903–904, 920–925; 607/32, 60, 30–31; 340/573.1–576

(56) References Cited

U.S. PATENT DOCUMENTS

| | | |
|---|---|---|
| 3,646,606 A | 2/1972 | Buxton et al. |
| 4,265,241 A | 5/1981 | Portner et al. |
| 4,360,019 A | 11/1982 | Portner et al. |
| 4,373,527 A | 2/1983 | Fischell |
| 4,443,218 A | 4/1984 | DeCant, Jr. et al. |
| 4,494,553 A | 1/1985 | Sciarra et al. |
| 4,871,351 A | 10/1989 | Feingold |
| 4,958,645 A | 9/1990 | Cadell et al. |
| 5,100,380 A | 3/1992 | Epstein et al. |
| 5,153,584 A | 10/1992 | Engira |
| 5,307,817 A | 5/1994 | Guggenbuhl et al. |
| 5,319,355 A | 6/1994 | Russek |
| 5,381,798 A | 1/1995 | Burrows |
| 5,410,471 A | 4/1995 | Alyfuku et al. |
| 5,415,181 A | 5/1995 | Hogrefe et al. |
| 5,416,695 A | 5/1995 | Stutman et al. |
| 5,421,343 A | 6/1995 | Feng |
| 5,452,356 A | 9/1995 | Albert |
| 5,458,123 A | 10/1995 | Unger |
| 5,462,051 A | 10/1995 | Oka et al. |
| 5,481,255 A | 1/1996 | Albert et al. |
| 5,534,851 A | 7/1996 | Russek |
| 5,536,084 A | 7/1996 | Curtis et al. |
| 5,537,459 A | 7/1996 | Price et al. |
| 5,544,661 A | 8/1996 | Davis et al. |
| 5,553,609 A | 9/1996 | Chen et al. |
| 5,558,640 A | 9/1996 | Pfeiler et al. |
| 5,569,186 A | 10/1996 | Lord et al. |
| 5,576,952 A | 11/1996 | Stutman et al. |
| 5,594,786 A | 1/1997 | Chaco et al. |
| 5,617,871 A | 4/1997 | Burrows |
| 5,626,151 A | 5/1997 | Linden |
| 5,630,710 A | 5/1997 | Tune et al. |
| 5,652,570 A | 7/1997 | Lepkofker |
| 5,657,236 A | 8/1997 | Conkright |
| 5,678,562 A | 10/1997 | Sellers |
| 5,699,038 A | 12/1997 | Ulrich et al. |
| 5,703,786 A | 12/1997 | Conkright |
| 5,704,366 A | 1/1998 | Tacklind et al. |
| 5,713,350 A * | 2/1998 | Yokota et al. .................. 395/2 |
| 5,713,856 A | 2/1998 | Eggers et al. |
| 5,718,234 A | 2/1998 | Warden et al. |
| 5,807,336 A | 9/1998 | Russo et al. |
| 5,822,544 A * | 10/1998 | Chaco et al. .................. 395/2 |
| 5,827,180 A | 10/1998 | Goodman |
| 5,855,550 A | 1/1999 | Lai et al. |

(List continued on next page.)

Primary Examiner—Kevin Shaver
Assistant Examiner—Michael Astorino
(74) Attorney, Agent, or Firm—Reinhart Boerner Van Deuren, s.c.

(57) ABSTRACT

An integrated medical monitoring and alert system for monitoring a medical therapy delivered to a patient and patient physiological parameters is disclosed. The medical monitoring system preferably includes a central monitoring system and one or more of a therapeutic device, a patient monitor, and an integrated alert system. The components are linked together through a bi-directional communications system which can comprise a wireless communications link to provide for mobile patients and communications to remote caregivers.

34 Claims, 11 Drawing Sheets

U.S. PATENT DOCUMENTS

| | | |
|---|---|---|
| 5,871,465 A | 2/1999 | Vasko |
| 5,877,675 A | 3/1999 | Rebstock et al. |
| 5,885,245 A | 3/1999 | Lynch et al. |
| 5,895,371 A | 4/1999 | Lavitas et al. |
| 5,944,659 A * | 8/1999 | Flach et al. .................. 600/300 |
| 5,959,529 A | 9/1999 | Kail, IV |
| 5,961,448 A | 10/1999 | Swenson et al. |
| 6,213,942 B1 * | 4/2001 | Flach et al. .................. 600/300 |

* cited by examiner

Fig. 4 (CENTRAL MONITORING SYSTEM)

MEDICAL MONITORING AND ALERT SYSTEM FOR USE WITH THERAPEUTIC DEVICES

The present invention relates generally to medical monitoring and alert systems, and more specifically to a medical monitoring and alert system for monitoring the status of therapeutic devices such as intravenous infusion pumps, ventilators, and patient warming devices and providing alert status information to remote caregivers via bi-directional wireless communications. The medical monitoring and alert system can also be used to control the operation of the therapeutic devices through wireless communications from a central monitoring system, monitor physiological parameters and provide bi-directional communications with an alert system.

BACKGROUND

Electronic devices for delivering a medical therapy are well known in the art. Among these devices are intravenous infusions pumps (IV Pumps), ventilator support devices (ventilators), hemodialysis machines, and patient warming/cooling systems.

Electronic therapeutic devices frequently include an audio or visual alarm or alert system to provide an indication to a caregiver when attention is required. In some cases, these devices also include an analog output port that can be connected to a simple "Nurse Call" system, such as a remote audio alarm or a lamp illuminated outside the patients' room. More recently, therapeutic devices have included an RS-232 serial port for communicating various therapy status data and alarm data to an external system. The data is often transmitted to an existing computer network in a clinical setting, and frequently to computerized patient record devices to collect status information. While these known therapeutic devices are very effective in some applications, they also suffer from some notable disadvantages.

One problem associated with prior art patient monitor/therapeutic device combinations is that the devices are not sufficiently mobile for many clinical settings. In many cases, the patient monitors are large, non-mobile, fixed units. Those which are sufficiently small to allow for mobile applications are generally connected through an RS-232 port or other hard-wired communications port to an external network or other system. Whenever a patient must be moved, therefore, the monitor must be disconnected and reconnected at the new location. Furthermore, a patient cannot move throughout a care facility while being monitored. These units, therefore, are problematic in many clinical settings.

Another problem associated with prior art therapeutic devices is that they often include audio or visual alarms or alert signals that require the caregiver to be near the device when an emergency occurs. Visual and audio alert signals are generally sufficient when used in an intensive care unit or other closely watched hospital setting. In these environments, the caregiver is always within range of any alarms that the therapeutic device generates. These devices, however, are not sufficient for use in general clinical settings where a small number of nurses or other caregivers are monitoring a large number of patients, because visual and audio alert signals do not provide a means for notifying a remote caregiver of an alert situation.

Additionally, the alert or alarm signals coupled to prior art devices generally require a manual confirmation that an alert or alarm signal has been received. The confirmation may require the activation of a switch, a telephone call, or other manual input. In other cases, the alert or alarm signal is unidirectional. In these cases, the alarm or alert signal can continue indefinitely without receiving the response of a caregiver.

Furthermore, existing patient monitor/therapeutic device combinations generally cannot control the therapy delivered to a patient from a remote location. Therefore, when a change in a patient's condition is detected, a caregiver must physically move to the patient's bedside. This system is inefficient in many clinical settings where a limited number of personnel are monitoring and providing medical care to a number of patients.

There remains a need, therefore, for an integrated medical monitoring and alert system capable of optionally monitoring both the therapy delivered to and the physiological parameters of a mobile or ambulatory patient while providing an alarm or alert signal to remote caregivers. Therapy delivery, monitoring, and alert signal devices would preferably be coupled to the monitoring system via hardwired or wireless communications links, depending on the required application. Monitoring information would preferably be transmitted via a wireless communication link to allow for monitoring of mobile patients. The communications link would preferably also be bi-directional to provide a means for acknowledging the receipt of an alert or alarm signal, and therefore a means of determining that an alert condition has been attended to or resolved. Furthermore, bi-directional communications allow for remote control of therapy delivery and physiological monitoring parameters from an external device. Preferably, the medical monitoring system would include a patient monitor for monitoring and transmitting patient vital sign data, and a central monitoring system located at a nurse's station or other centralized location to provide a remote monitor of patient therapy status and alert conditions. The central monitoring system would preferably also provide a storage location for maintaining a database of patient therapy status data, alert conditions, vital sign parameters, and therapy applied data to provide a total record of patient care. The central monitoring system would also preferably be linked to an overall hospital information system for maintaining overall patient records, which could include clinical data in addition to insurance data, physician data, pharmaceutical data, and other medical information.

SUMMARY OF THE INVENTION

Accordingly, it is an object of the invention to provide an integrated medical monitoring and alert system which can be used to monitor a medical therapy delivered to a patient and provide therapy status data, physiological data, and alert data to a remote caregiver via bi-directional communications.

It can be another object of the invention to provide a medical monitoring system optionally comprising physiological monitoring, therapy delivery, and alert devices which can be selectively configured to provide a customized system for a given medical monitoring situation.

It can be another object of the invention to provide a medical therapy delivery system linked bi-directionally to both monitoring and alert condition devices.

It can be another object of the invention to provide a medical monitoring system comprising a communications network which can include both wireless bi-directional links and hardwired links between therapy delivery, monitoring, storage and alert components such that each of the components of the system can selectively communicate with each of the other components of the system.

It can be another object of the invention to provide a medical monitoring system capable of monitoring a medical therapy delivered to mobile patients and capable of providing alert condition data to remote caregivers.

It can be another object of the invention to provide a bi-directional alert and monitoring system coupled to a therapy delivery system.

It will be understood by those skilled in the art that one or more aspects of this invention can meet certain objectives, while one or more other aspects meet certain other objectives. Each objective may not apply equally, in all instances, to every aspect of the invention. As such, the objects can be viewed in the alternative with respect to any one aspect of the present invention.

The medical monitoring system of the present invention preferably comprises a central monitoring system for monitoring the therapy and physiological status of a number of patients from a nurse's station or other centralized monitoring location and at least one of a therapeutic delivery device, a local patient monitor for monitoring therapy and physiological parameters, and an integrated alert system for providing both patient physiological and therapy status data and alert condition data to remote caregivers. Communications between the various components of the system are preferably provided through a bi-directional communications network, thereby allowing interaction between any of the various components. For example, due to the bi-directional communication system, the alert system can notify the central monitoring system when an alert signal has been received, thereby assuring the clinical personnel at the central station that an alert condition is being attended to. Furthermore, in some embodiments of the invention, the central monitoring system can be used to select the output parameters of the therapeutic device. The patient monitor, central monitoring systems, and remote access devices are preferably coupled together through a bi-directional communications network comprising both a hardwired segment and a wireless segment. Each of the component parts of the system can communicate to another component of the system through a communications link, employing either the hardwired segment, the wireless segment, or both. Therefore, rapid delivery of therapeutic data, physiological parameters, and alert conditions can be communicated quickly through and even outside a care facility.

In operation, therapy status data from the therapeutic device such as an intravenous infusions pump (IV Pump), ventilator support device (ventilator), hemodialysis machine, or patient warning/cooling system, can be regularly communicated to the patient monitor through a communications port which can be linked to a wireless communication segment, an RS-232 serial connection, or other hardwired or wireless network connection. At the patient monitor, the therapy status data can be displayed, stored in memory, or both. The patient monitor can further transmit the therapy status data to the central monitoring system where the data, again, can be displayed, stored, or transmitted to a data storage system, as will be discussed below. Optionally, the patient monitor can also monitor, store, and transmit patient physiological parameters.

When a therapy alert condition occurs, a medical alert signal can be sent from the therapeutic device to the patient monitor. The patient monitor can also provide alert condition signals related to physiological conditions. The patient monitor preferably transmits the alert condition data to the central monitoring system along with patient physiological parameter information, and therapy status information as part of the normal data communications structure used to transmit this information. These medical alerts can be reviewed by a caregiver at the central monitoring system, or sent out automatically as selected by the user. The latter mode permits unattended medical alerts to be sent to remote caregivers when the central monitoring system is unmonitored.

The alert signal can be transmitted to an alert system which preferably comprises a number of remote access devices carried or located near caregivers. The remote access devices communicate bi-directionally with the central monitoring system. Preferably, therefore, once an alert signal has been received by a caregiver, an acknowledgement signal can be sent by the remote access device to the central monitoring system. In the event that no acknowledgement is received, the central monitoring system can alert additional caregivers until an acknowledgement is received and the alert condition is resolved. Although the remote access devices preferably comprise pagers, other devices including telephones, handheld computers, personal digital assistants (PDAs) and personal computers can also be used.

Preferably, the patient monitors and the central monitoring systems are each capable of storing patient therapy, patient physiological data, and alert status data for later retrieval and display by medical personnel. To ensure accurate entry and retrieval of stored patient data, the patient monitors, central monitoring systems, alert system remote access devices, and therapeutic devices can all include electronic data entry devices such as barcode scanners. The data entry devices can be used to identify the patient, the caregiver, medications, solutions, and devices. This identification information can be stored as part of an overall patient record database.

Furthermore, the information communicated to the central station from the therapeutic device is preferably shared with an auxiliary storage component or computerized database system such as hospital information system (HIS) programs and computers. This shared data allows other external systems to monitor and track this data for clinical record keeping and also for billing, central supply ordering, pharmacy tracking etc. Interaction with pharmacy computer systems allows for review of currently infused drugs and solutions to determine whether a combination of pharmaceuticals being delivered to the patient may be affecting the condition of the patient. Any detected alerts from these pharmacy computer programs could be linked back to the central station via the HIS and be supplied as an alert conditions triggering a signal to the remote access devices. Thus the caregiver would have rapid notification of potential complications as detected by these pharmacy systems.

In some embodiments of the invention, the therapeutic device can communicate directly with the central monitoring system. In these embodiments, the therapeutic device preferably communicates directly with the central monitoring system through the wireless segment of the communications network. The wireless communications capability can be added to the therapeutic device by means of commercially available RF communication modules or through a custom designed integral module coupled to the therapeutic device.

As noted above, because the communications technology used in this system is bi-directional, the central monitoring system can be used to remotely control the therapeutic device or the patient monitor in some applications. In these applications, the central monitoring system can be used to change the delivery parameters, reset alert conditions, select monitoring parameters, and provide delivery timing data. The ability to remotely control the therapeutic device and patient monitors increases efficiency in staff utilization and reduces time requirements in patient care. In these applications, all changes to the therapeutic device settings are part of the patient record. Therefore, all related status information can be presented as a complete patient trend record documenting the patients' condition.

Because wireless bi-directional communications can be employed between the therapeutic device, a patient monitor, and a central monitoring system, the patient may be mobile while being safely monitored for both vital signs and therapeutic device status. Because patient mobility is important in recovery, all patients are encouraged to become mobile. The ability to monitor the vital signs and health of an ambulatory patient therefore offers a major advantage over prior art systems.

Other advantages and features of the invention, together with the organization and manner of operation thereof, will become apparent from the following detailed description when taken in conjunction with the accompanying drawings wherein like elements have like numerals throughout the drawings.

DETAILED DESCRIPTION OF THE PREFERRED EMBODIMENTS

Figure 1:
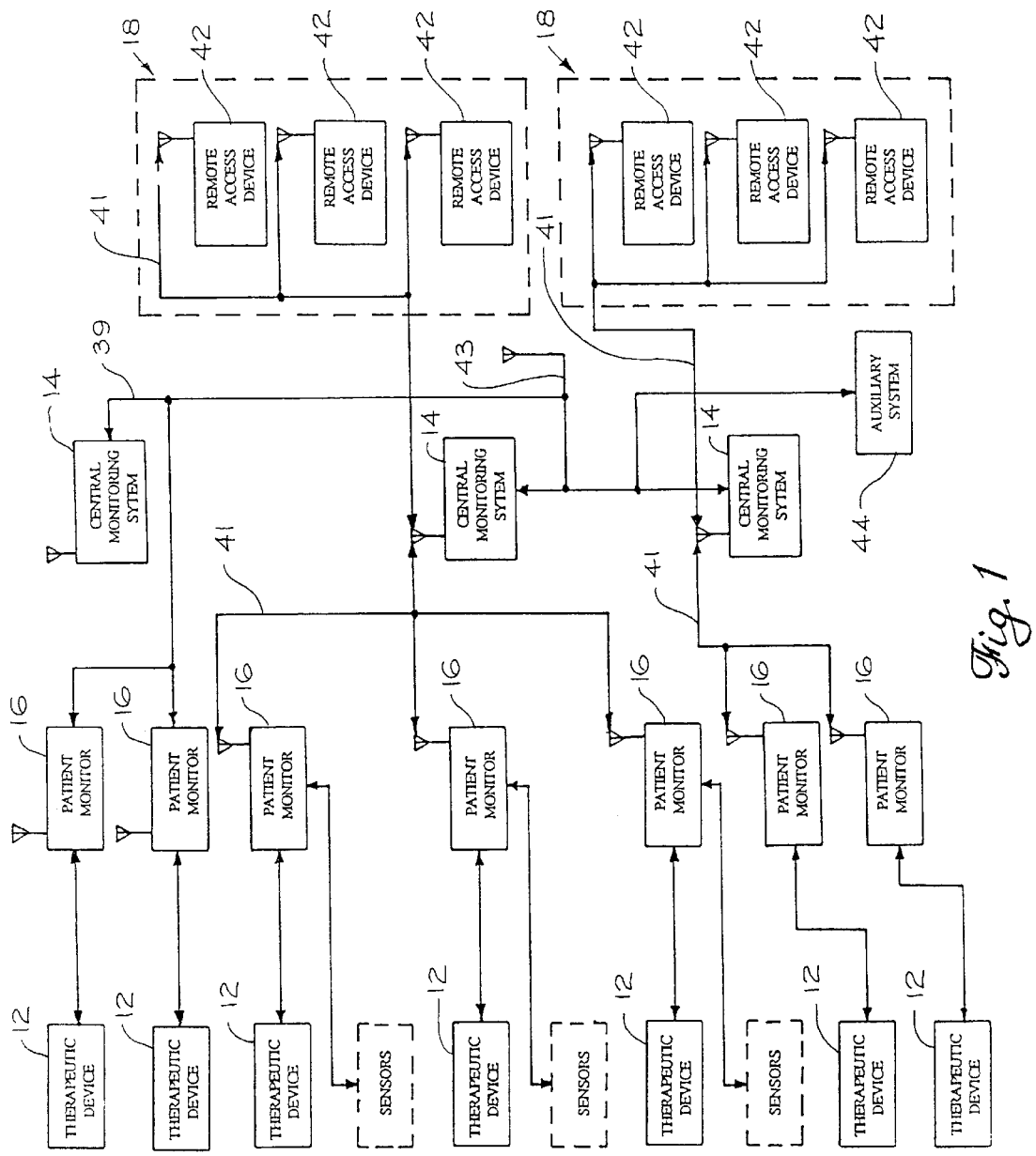
FIG. 1 is a block diagram of a medical monitoring and alert system constructed in accordance with one embodiment of the invention.

Referring to the figures and more particularly to FIG. 1, a medical monitoring system constructed in accordance with one embodiment of the invention is shown generally at 10. The medical monitoring system 10 comprises at least one of a therapeutic device 12, a patient monitor 16, or an alert system 18 and at least one central monitoring system 14, (hereinafter, the components of the medical monitoring system 10). The alert system 18 preferably comprises a plurality of remote access devices 42. The components of the medical monitoring system 10 can be selected by the user as required for a particular medical monitoring situation.

The components of the medical monitoring system 10 can be coupled together through a bi-directional communications network 37 comprising a hardwired segment 39 and a wireless segment 41. The hardwired segment 39 is preferably coupled to the wireless segment 41 through one or more access points 45. The access points 45 couple the hardwired segment 39 to the wireless segment 41 through antennas which transmit a signal to the wireless segment 41 of the communications network. It will be understood by those of ordinary skill in the art that any of a number of wireless communications systems including RF, IR, and other known systems can be used for the wireless segment 41 of the communications network 37. Furthermore, any of a number of known hardwired communication systems including local area networks, wide area networks, and modem links can be used for the hardwired segment 39. Additionally, in some cases, it will be advantageous to employ more than one type of hardwired segment 39 and/or more than one type of wireless communication segments 41, as will be described more fully below. In some applications, therefore, the communications network 37 can comprise only a wireless segment 41 or only a hardwired segment 39, depending on the application. Hereafter, a "link" shall be any point to point communication between components of the system over the communications network, whether through the wireless segment 41, the hardwired segment 39, or both.

Each of the components of the medical monitoring system 10 include a network interface 20 which includes either a communications port for communicating through the wireless segment 41 of the communications network 37, a communications port for communicating through the hardwired segment 39 of the communications network 37, or both. Each of the components of the medical monitoring system 10 further includes a unique identification code which allows other components of the medical monitoring system to identify (1) the type of component which is transmitting a signal; and (2) the specific component transmitting the signal. Each of the components of the medical monitoring system 10, therefore, can be linked to another of the components of the medical monitoring system through either the hardwired segment 39, the wireless segment 41, or both, and each component of the medical monitoring system can communicate with other components of the system. Therefore, as noted above, various components of the system can be selected and linked together as required for a particular monitoring application. In some applications, for example, the system may comprise a central monitoring system 14 and a patient monitor 16. If therapy delivery is required, a therapeutic device 12 can be linked to the system. Furthermore, an alert system 18 can also be linked to the system to provide alert condition and status data to remote caregivers, as required.

Figure 2:
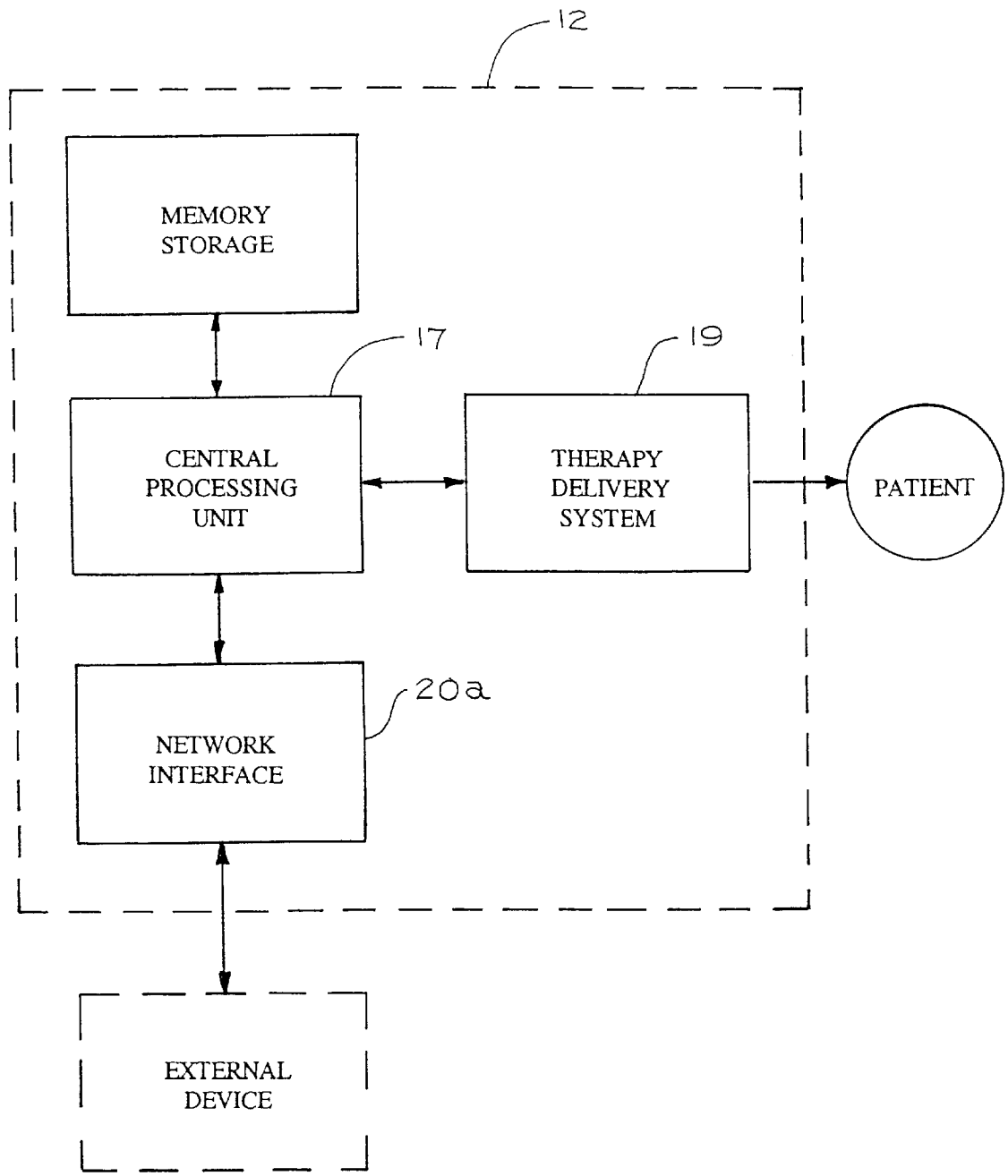
FIG. 2 is a block diagram of a therapeutic device as shown in FIG. 1.

Referring now to FIG. 2, a block diagram illustrating the therapeutic device 12 is shown. The therapeutic device 12 can be any of a number of implements for delivering a medical therapy to a patient. Examples of such devices are intravenous pumps (IV pumps) for delivering fluids or drug therapies; respirators; and patient/bed warming devices. Generally, however, all types of therapeutic devices 12 include a control component 17 or central processing unit for controlling the delivery of a given therapy to a patient and for controlling communications to external devices; a network interface 20a for communicating therapy status data and alert condition data to and receiving control commands from external devices; and a therapy delivery system 19, which may comprise a pump, valve, heating element, or other therapy device depending on the application. In some applications, the therapeutic device 12 can also include keypad entry devices, electronic data entry devices such as barcode scanners, and display units for entering desired delivery parameters and displaying medical delivery parameters and alert conditions.

Therapy status data and alert condition data are collected by the control component 17 and can be stored in a memory component in the therapeutic device 12. This data can be transmitted to other components, and particularly to the patient monitor 16, through the network interface 20a. Communications with the therapeutic device 12 can be unidirectional, wherein the therapeutic device 12 transmits therapy status data and alert condition data to external devices, or bi-directional, such that the external device may communicate control commands to the therapeutic device, as will be described below.

Transmitted therapy status data from the therapeutic device 12 generally comprises ongoing therapy parameters. For example, in the case of an IV pump, therapy status data can include information such as infusion rate, volume infused, and volume to be infused. Alternatively, in the case of a ventilator, therapy status data can include parameters such as: breath rate set, breath rate actual, tidal volume (volume of the breath measured in metric milliliters/liters), minute volume (the total volume of breaths for 1 minute), I/E ratio (ratio of time of inspired breathing Vs expired), amount of PEEP (Positive End Expiratory Pressure) if any, airway pressures, airway flow/volume information and in some cases oxygen and/or carbon dioxide measurement. For patient heating/cooling devices, therapy status data may include data such as the expected temperature and actual temperature of a patient. Hemodialysis machines can provide status parameters including water velocity, concentrate level, time, arterial and venous pressure, and temperature.

Alert condition data, on the other hand, generally includes equipment maintenance or failure data, and can also include medical alert data. For example, the alert data can include equipment status information such as "low battery" signals, and "communications interrupted" signals, as well as delivery status information such as "empty container" and "air present" signals. In the case of hemodialysis machines in particular, the alert data can include water quality conditions, low pressure, blood leak detection, air in blood, low reverse osmosis water velocity and other alert conditions.

Figure 3:
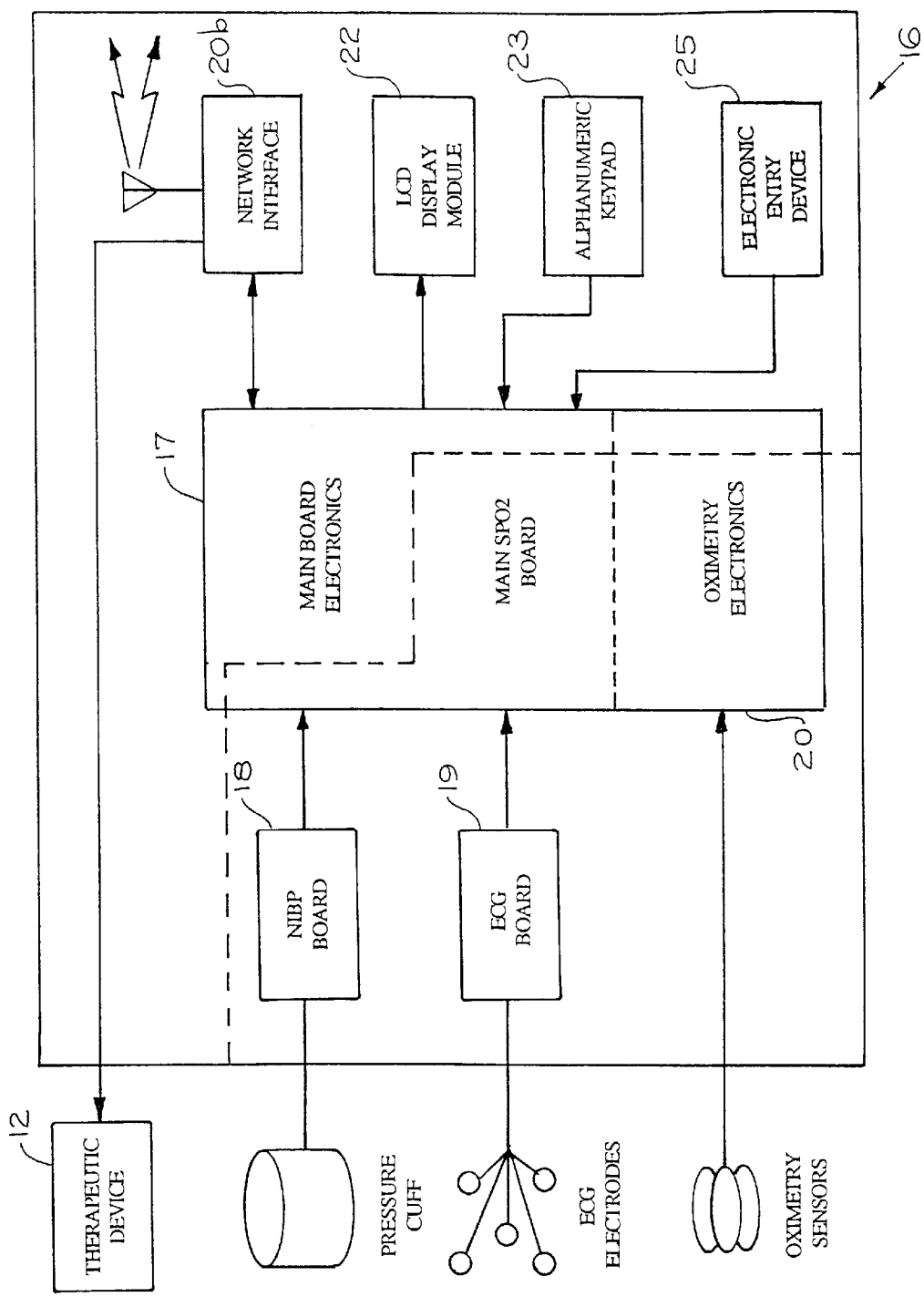
FIG. 3 is a block diagram showing one preferred embodiment of a patient monitor of the present invention.

The patient monitor 16 is preferably located near the patient, and can, for example, be located at the patient's bedside or coupled directly to the patient. Referring now to FIG. 3, a block diagram of a patient monitor constructed in accordance with one preferred embodiment of the present invention is shown. The patient monitor 16 includes a network interface 20b which provides a bi-directional communication link to other components of the medical monitoring system 10. Preferably, the patient monitor 16 monitors therapy status data and alert condition data from the therapeutic device 12. In some applications, however, the patient monitor 16 also includes the capability to monitor a number of physiological parameters. In these applications, the patient monitor 16 can be used to track blood oxygenation, ECG, and NIBP parameters, as is shown in FIG. 3. These patient physiological parameters and vital sign statistics can be stored in the patient monitor 16 and transmitted to the central monitoring system 14. In the central monitoring system 16, the patient physiological parameter data is preferably stored with simultaneous therapy status data and alarm conditions, thereby providing a complete record of patient reaction to a given therapy. The patient monitor 16 can also provide alert condition data based on physiological parameters to the central monitoring system 14 and to the alert system 18.

Preferably, the patient monitor includes a display 22 for optionally displaying therapy status, physiological parameter, and alert condition data to a local caregiver, and an alphanumeric keypad 23. The user interface (comprising the display and keypad) permits the caregiver to locally select patient monitoring conditions, including the selection of therapy delivery parameters, vital signs to be monitored; the adjustment of local display features including waveform selection, scaling, and sweep speed; and the transmission of command data to the central monitoring system 14 to initiate functions such as remote printing or to alert personnel associated therewith. In the event that a patient moves outside of the wireless communications range of any central station 14, this user interface permits the caregiver to operate the monitor locally like a conventional bedside monitor.

The patient monitor 16 can further comprise an electronic data entry device such as an electronic entry device 25. The electronic entry device 25 allows a user to scan data such as patient identification, drug therapy information, lab testing information, and activity testing information directly into the monitor, thereby preventing potential errors caused by manual data entry. Furthermore, this information can be transmitted to the central monitoring system 14 or other components in the system and can be accessed by caregivers who require information about a specific patient by scanning a bar code on a chart or other documentation. The electronic entry device 25 can be a bar code scanner, retinal scanner, or other types of devices.

Figure 4:
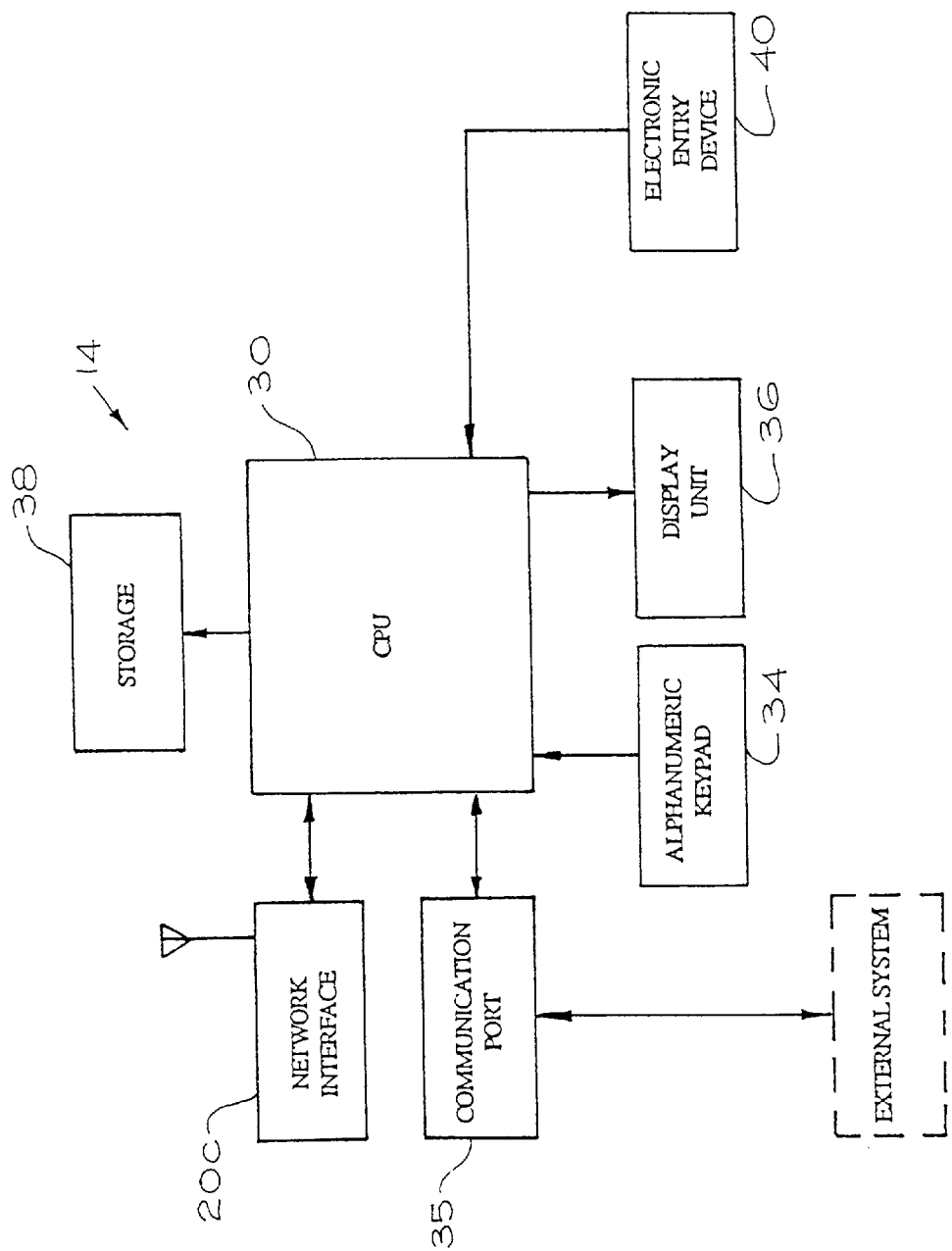
FIG. 4 is a block diagram showing one preferred embodiment of a central monitoring system constructed in accordance with the present invention.

The central monitoring system 14 is generally positioned in a location remote from patients, such as a nurse's station or other centralized monitoring location in a clinical setting. Referring now to FIG. 4, the central monitoring system 14 generally comprises a central processing unit 30, a network interface 20c, an optional keyboard 34 for data entry, a display unit 36 with optional touch screen, and a memory storage component 38. Preferably, the central monitoring system 14 also comprises at least one communications port 35 for delivering data to external devices not equipped with a network interface. Normally, however, devices such as printers, strip chart recording devices, and auxiliary systems 44 would utilize the network interface 20c.

The central monitoring system 14 can communicate with one or a plurality of patient monitors 16 through the network interface 20c, and therefore can collect and display information regarding a number of patients on the display unit 36. Furthermore, the central monitoring system 14 can store patient data and perform calculations on the stored data to provide trending data, records of physiological parameter values versus therapy status and event status, waveform analyses, and various other patient data. The central monitoring system 14 can further examine and filters alert condition data transmitted from the therapeutic device 12 and patient monitor 16 to provide an alert signal through the network interface 20c to the alert system 18, as will be described more fully below. In some embodiments, the central monitoring system 14 can also control parameters relating to the delivery of medical therapy such as the ability to select rate and total volume of an IV delivery, select between or selectively activate therapy devices, and select between a number of pumps to provide a sequenced drug delivery. Preferably, the central monitoring system 14 also controls the monitoring and display of physiological parameters at the patient monitor 16. The bi-directional communication capability of the patient monitors 16 of the invention make it possible for the central station 14 to select, per patient and at any time, the subset of available waveforms and vital signs data most appropriate for remote display, select the data sample rates and select display and other monitoring parameters.

Figure 5:
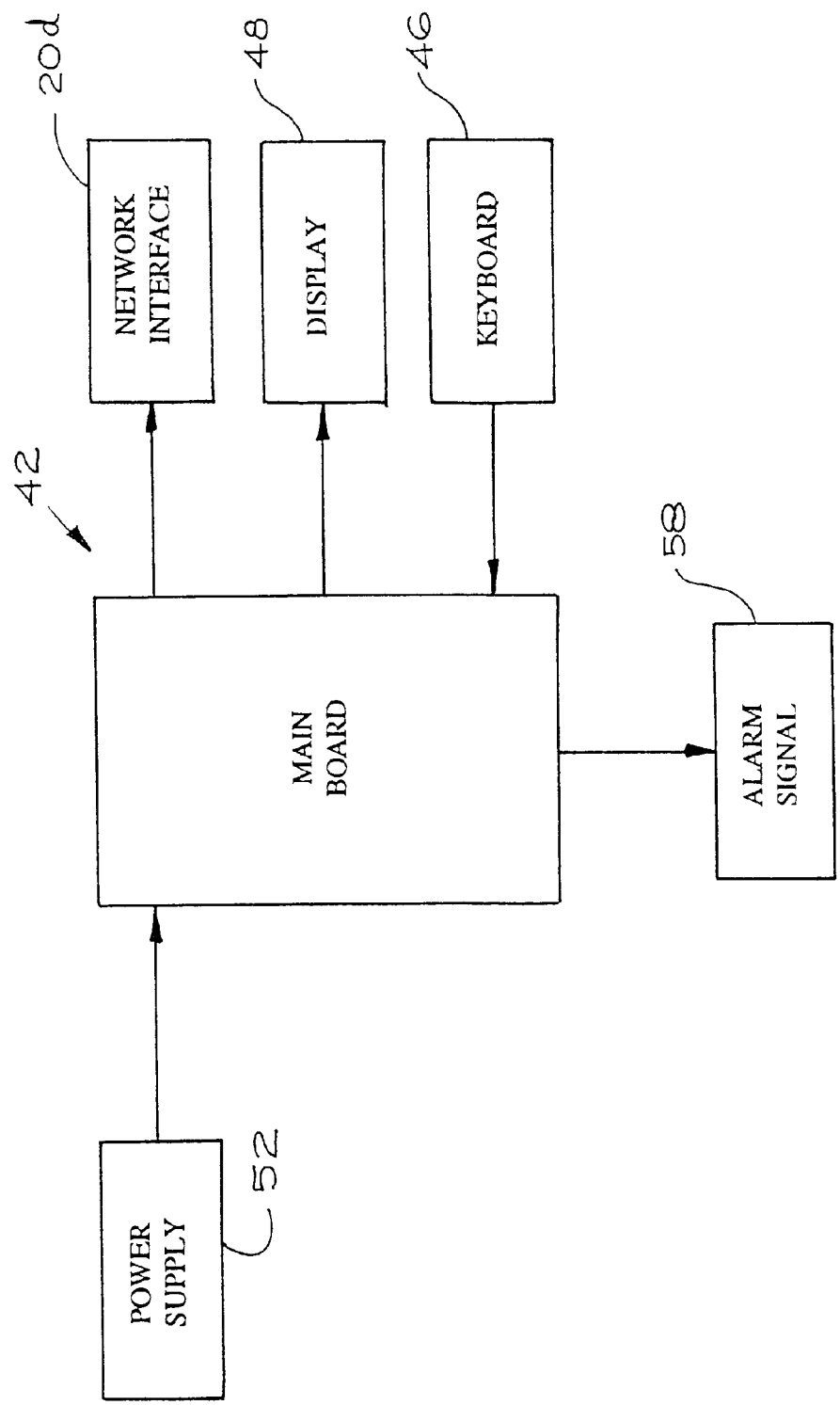
FIG. 5 is a block diagram of a remote access device constructed in accordance with the present invention.

Referring now to FIG. 1, the alert system 18 can comprise at least one remote access device 42 and preferably comprises a plurality of remote access devices 42. The remote access devices 42 are carried by caregivers for purposes of receiving alert signals, requesting and receiving medical data, and generally tracking patient performance as will be described more fully below. The remote access devices 42 (FIG. 5) require a network interface 20d for coupling the remote access device to the communications network 37, an alarm signal 58, a power supply 52 and preferably a display 48 and keyboard 46 or other electronic entry device. Other components and features may vary, depending on the expected application. Examples of remote access devices 42 includes pagers, telephones, handheld computers, and personal data assistants (PDAs). Preferably, the remote access device includes one or more of the following: text/graphical display; touch screen; keypad; microphone; speaker; or bar code scanner.

The remote access devices 42 are preferably coupled to other components of the medical monitoring system through the wireless segment 41, thereby allowing for a mobile caregiver to provide an acknowledgement signal from the remote access device 42 to end a given alert condition signal. However, in some applications, and particularly in the case of remote access devices 42 which comprise laptop computers, it can be advantageous for the user to connect to the communications network 37 through the hardwired segment 39. Furthermore, remote access devices 42 which would normally be linked to the hardwired segment 39 of the communications network 37, can be fitted with wireless modems and other devices to allow communications through the wireless segment 41.

Generally, the central monitoring system 14 is fixed, and is linked to other components through the hardwired segments 39. The patient monitors 16 are preferably mobile to allow for ambulatory patients, and therefore communicate through the wireless segment 41 of the communications network 37. The remote access devices are also preferably mobile to provide a means for contacting caregivers throughout a facility, and therefore also preferably communicate through the wireless segment 41 of the communications network 37. However, it will be apparent that the links between various components can be made through the communications network in a number of different ways depending on the application. For example, in temporary installations, it may be preferable to connect the central monitoring system 14 to other components entirely through the wireless segment 41 of the network. Also, in some cases, stationary patient monitors 16 may be preferable. Furthermore, a remote caregiver may want to connect to the medical monitoring system from a remote location through the hardwired segment 39. Again, the system can be configured to employ various types and numbers of components and various communications links as required by a particular medical monitoring and therapy situation.

Figure 6:
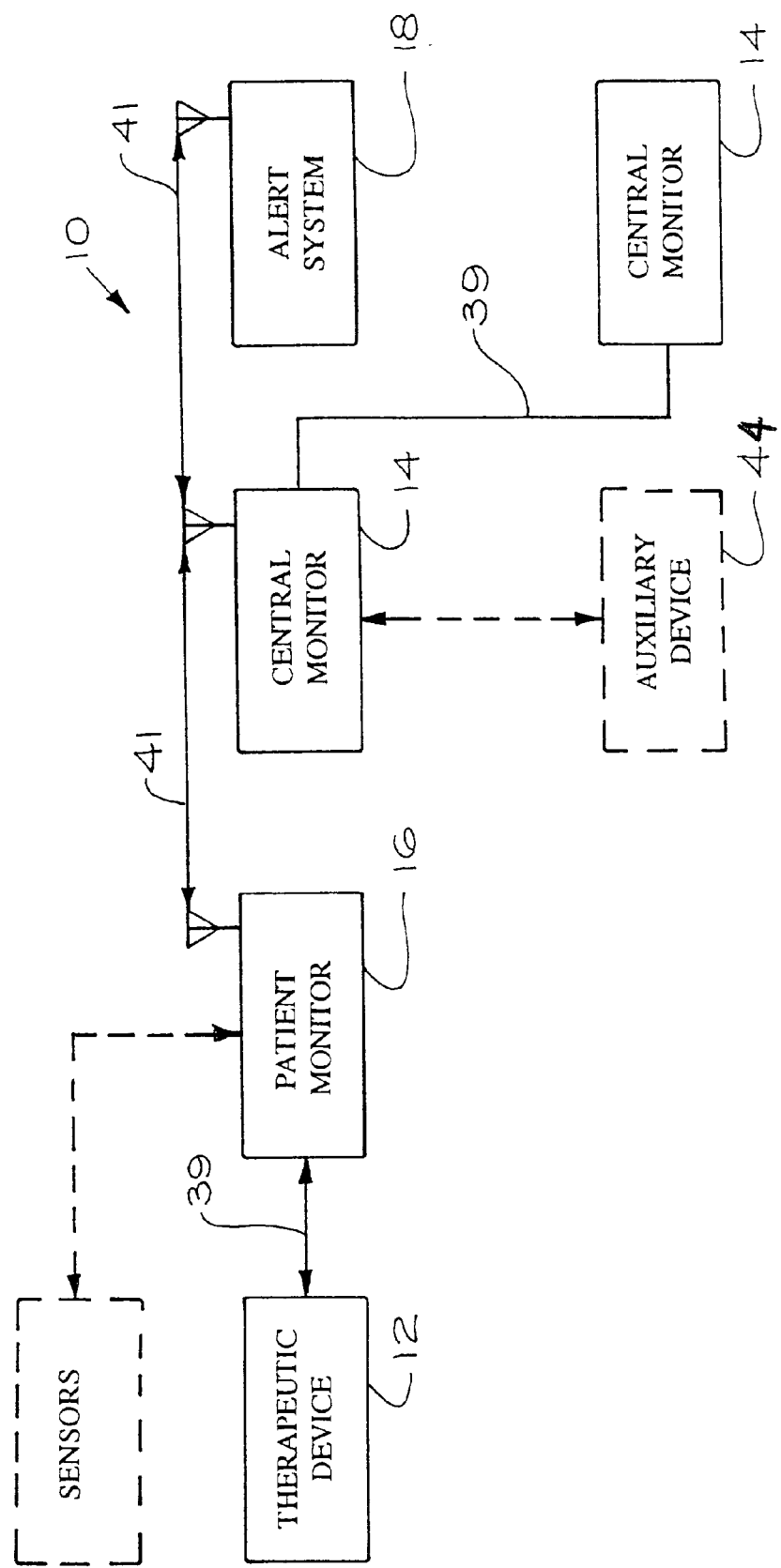
FIG. 6 is a block diagram of a medical monitoring system constructed in accordance with a preferred embodiment of the present invention.

Referring now to FIG. 6, one embodiment of a medical monitoring system constructed in accordance with the present invention is shown. In this embodiment, the therapeutic device 12 is preferably linked to the patient monitor 16 through a hardwired communications link, preferably an RS-232 communications link. Therefore, the network interface 20a can comprise hardware for coupling to an RS-232 hardwired link. Therapy status data and alert condition data is delivered to the patient monitor 16 via the RS-232 link. The RS-232 link can be a separate communications link connected to the communications network only through the patient monitor 16. Although a specialized therapeutic device 12 can be constructed for use in this preferred embodiment, a number of existing commercial products can also be used. Examples of available IV products include the IMED Gemini Pump and the IVAC Signature Pump. These pumps include an RS-232 serial communications port that provides the necessary therapy status and alert status data to external devices, and can be readily connected to the patient monitor 16 as will be described below. While a bi-directional communications link is preferred, a unidirectional communications link from the therapeutic device 12 to the patient monitor 16 can also be used.

The patient monitor 16 can be linked to the central monitoring system 14 through the wireless segment 41 of the communications network 37 to allow for patient mobility. The patient monitor 16 receives therapy status data from the therapeutic device over the RS-232 link described above, and transmits therapy status data, patient physiological parameter data, and alert condition data to the central monitoring system 14 through the wireless segment 41. In this embodiment of the patient monitor 16, therefore, the network interface 20b comprises both hardware to couple the device to an RS-232 link and a transceiver for transmitting and receiving communications over the wireless segment 41. Although a network interface has been described, the communications devices employed in the invention can comprise a transceiver for communicating with the communications network and separate device interface, such as the RS-232 link described, for communicating with the therapeutic device 12. The device interface can be a separate component of the system and, for example, coupled to the main circuit board of FIG.3.

The central monitoring system 14 can be linked to at least one patient monitor 16 through the wireless segment 41, to the alert system 18 through the wireless segment 41, and to one or more other central monitoring systems 14 through the hardwired segment 39 to provide an overall care network. The central monitoring also preferably comprises at least one communications port 35 for delivering data to external devices such as printers, strip chart recording devices, and auxiliary systems 44 which may lack a network interface. Therefore, the central monitoring system 14 comprises a centralized data collection station which can communicate with and control mobile patient monitoring, therapy delivery, and remote caregivers. The network interface 20c in this case will usually be a hardwire connection for coupling to the hardwired segment 39 and thus indirectly to the wireless segment 41.

Figure 7:
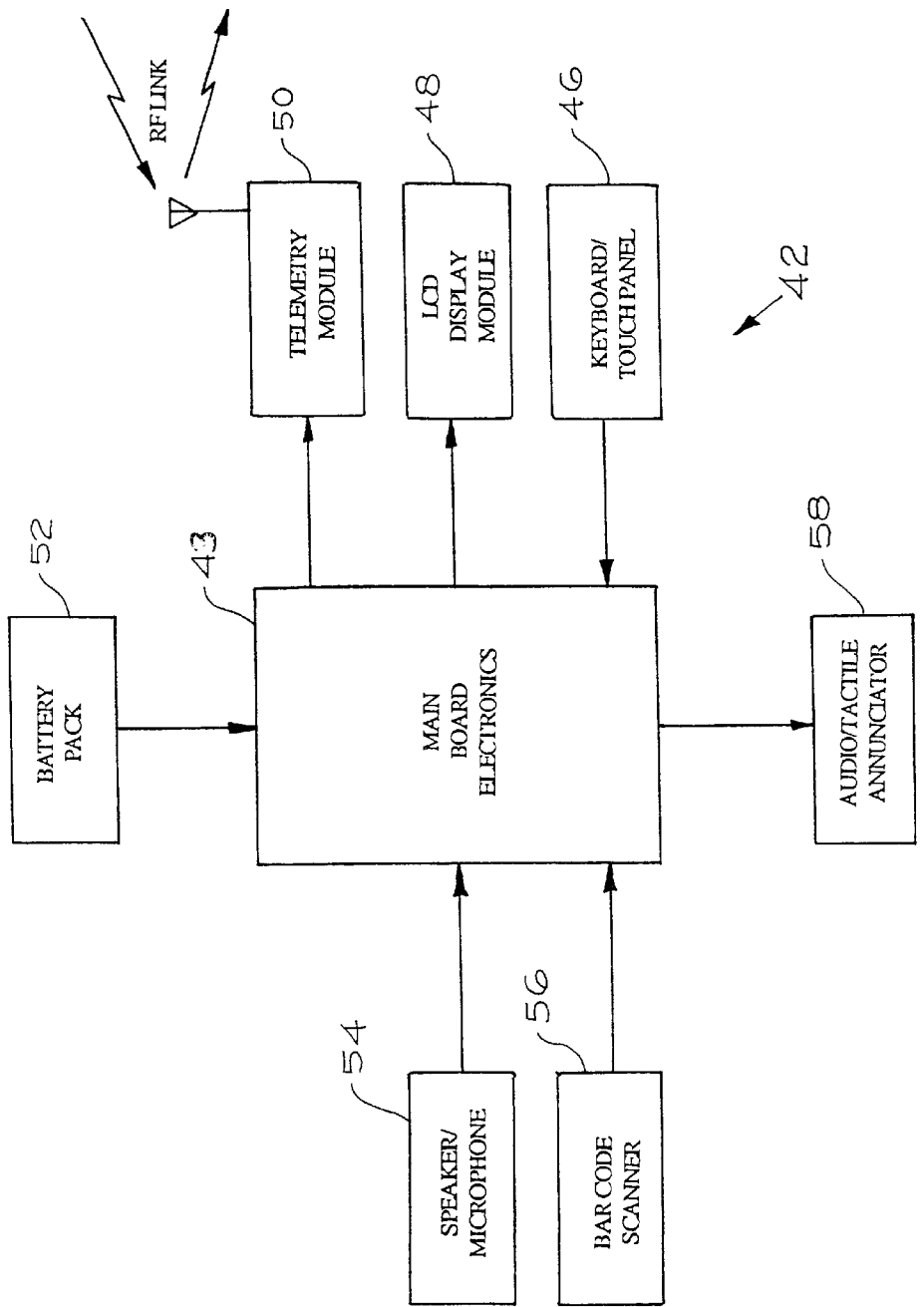
FIG. 7 is a block diagram of a remote access device constructed in accordance with an embodiment of the present system.
Figure 8:
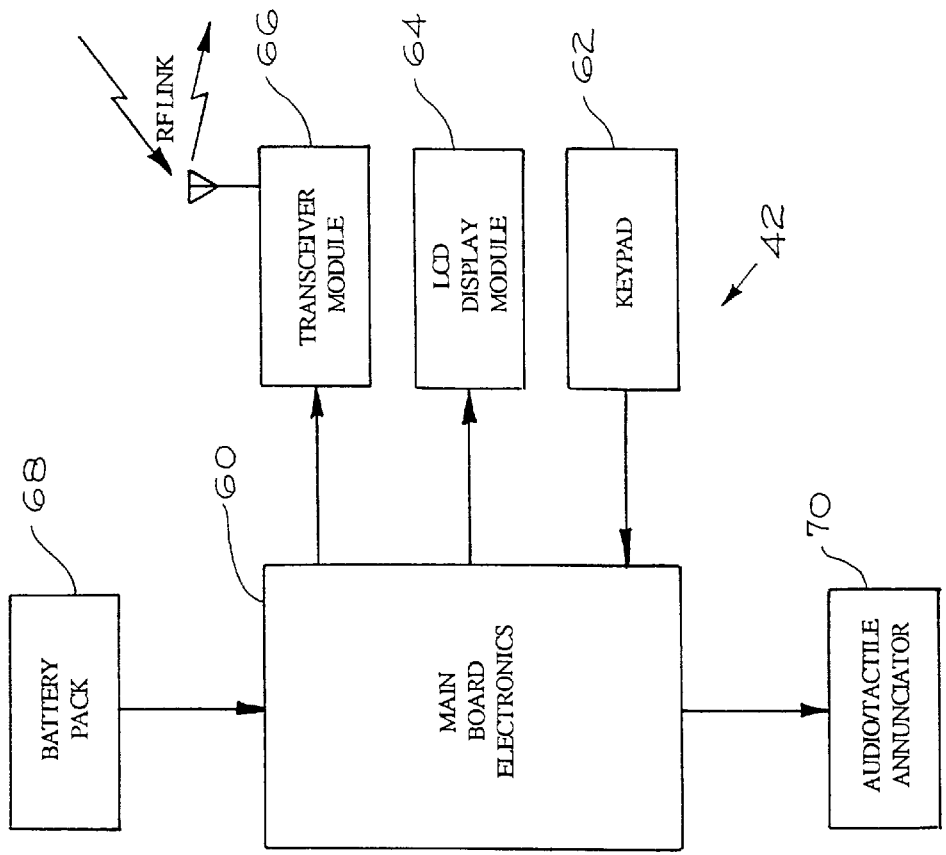
FIG. 8 is a block diagram of a remote access device constructed in accordance with an embodiment of the present system.

The alert system 18 preferably comprises a plurality of remote access devices 42. Referring now to FIGS. 7 and 8, two types of remote access devices 42 which can be employed in the preferred embodiment are shown. FIG. 7 shows a remote access device 42 comprising a hand-held computer or personal digital assistant (PDA). This remote access device preferably comprises a main electronics board 43 comprising a processor and a memory component; a keyboard 46 or other input device, such as a touch panel; a display module 48, which is preferably LCD but may comprise other types of known displays; a telemetry module 50 for communicating over the wireless communication segment; a battery pack 52; a microphone and speaker 54; a bar code scanner 56; and an audio/tactile annunciator 58, such as a vibrational device or an audio alarm.

FIG. 8 shows a simpler remote access device 42 similar to a traditional pager. This remote access device preferably comprises a main board 60, including a processor and a memory storage component; a keypad 62 or other input device; a display module 64; a transceiver module 66; a battery pack 68 or other power supply; and an audio/tactile annunciator 70. The remote access devices 42 can be selectively linked to at least one central monitoring system through the wireless segment 41.

In one embodiment, the hardwired segment 39 of the communications network 37 is an Ethernet backbone, and the wireless network component 41 is a spread-spectrum RF wireless LAN subsystem operating in the ISM band. All of the communications through the wireless segment 41 of the communications network 37 comprise bi-directional, spread-spectrum RF transmission of digital data which can include forward error correction. In spread spectrum technology, the RF frequency band is divided into a number of discrete sub-bands which are shared by all communication links in the system, which take turns operating in different channels for short periods of time. In frequency-hopping spread spectrum communications, the transmitters "hop" along a programmed sequence of frequency sub-bands in such a way as to avoid interference with each other. The hop sequences may be thought of as defining a set of non-interfering channels through time.

Furthermore, standard network protocols including TCP/IP and UDP can be employed to transfer messages over the network 37. These protocols, which are standard in computer networking, provide features for facilitating reliable communications. These include means of (a) uniquely identifying devices by address, (b) formatting messages for reliable transmission by means of sequence numbers, error detection and/or correction, and (c) enabling retransmission of missed messages.

Each central monitoring system 14 can receive a stream of messages from many sources at its network interface 20c. The individual messages, formatted in one of the aforementioned standard network protocols, contain all the address information necessary to identify the originating device, be it a patient monitor 16, remote access device 42, or therapeutic device 12. These addresses can be pre-assigned at installation of the patient monitoring system 10 or components thereof, or may be dynamically assigned as new devices request communications with the central monitoring system 14.

In operation, the therapeutic device 12 can be coupled to a patient to deliver a selected medical therapy to the patient. Hereinafter the therapeutic device 12 will be described as an IV pump, although, as noted above, the therapeutic device 12 could comprise any of a number of medical devices including respirators, warming devices, etc. As fluids or drugs are delivered to the patient, therapy status and alert condition data is transmitted through the network interface 20a to the patient monitor 16. As noted above, this connection is preferably an RS-232 serial communication link, but can be any of a number of different types of hardwired or wireless communication links. In this embodiment, the patient monitor 16 receives the information from the therapeutic device 12 through the network interface 20b, stores the data, and displays selected data to local caregivers. In applications where the patient monitor 16 also monitors physiological parameters such as an ECG or NIBP signal, vital sign data and therapy data are preferably stored in a single database to provide a trend analysis record, including a record of patient reaction to various therapies and alert conditions. In applications where the therapeutic device 12 includes a bi-directional communications port and can be controlled remotely, selected therapy delivery commands can also be stored for future reference.

From the patient monitor 16, data required or requested by the central monitoring system 14 is preferably transmitted through the wireless, segment 41 from the patient monitor 16 to the network interface 20c of the central monitoring system 14. As noted above, the central monitoring system 14 can also transmit data to the patient monitor 16 to select physiological or therapy delivery parameters to be monitored or displayed at the patient monitor 16, and to select parameters or data to be transmitted to the central monitoring system 14. From the central monitoring system 14, alert condition data can be transmitted to the alert system 18 through the network interface 20c, preferably utilizing the wireless segment communications network segment 41.

The alert system 18 preferably comprises at least one, and preferably a plurality of shared, remote access devices 42 carried by caregivers. The remote access devices 42 can request that specific data be transmitted back to the remote access device 42 for review by a caregiver. Alternatively, a central monitoring system 14 can transmit a message, typically an alert condition, to one or a group of remote access devices 42. The message can contain patient identification and location, therapy delivery status including volume and type of fluid or drugs being administered, alert information, numeric vital signs, and signal waveform data, or arbitrary contents entered through a keyboard or other input device. Because the remote access device preferably operates on the RF spread spectrum communication system, significantly more data can be transferred than in normal paging operations. The message can be initiated manually, in prompted fashion after an alert condition occurs, or automatically after an alert condition occurs. The message may contain static information suitable for a remote access device 42 with limited capabilities such as a pager, or dynamic information (e.g., continuously updated signal waveforms) requiring a more sophisticated remote access device 42.

The bi-directional communication link between the remote access device 42 and the central monitoring system 14 permits the central monitoring system 14 to recognize (a) whether the message successfully reached the target remote access device(s); (b) whether someone actuated the remote access device 42 and opened the message; and (c) whether the caregiver responded with a reply. The same communications technology permits the initiation of a message at the remote access device 42 directed to another remote access device 42 or to the central monitoring system 14, including forwarding of a received message. In this way, nurses or other personnel can be reached with critical information about a patient while performing activities in locations where they cannot view the central monitoring system 14. In some applications, free-form text may be entered at the remote access device 42 and forwarded to another component in the medical monitoring system, usually the central monitoring system 14. This free-form text can be used to provide a password to verify that a message has been received by the intended recipient.

As noted above, the central monitoring system 14 can communicate with auxiliary systems 44 to send and receive patient data for storage, display, analysis, and retrieval. The information transmitted may include patient demographics, clinical data, scheduling information, etc. The auxiliary system 44 may be a diagnostic workstation performing advanced analyses, a clinical information system, or an archival system. Communications may be via hardwired (e.g., serial or network) or wireless communications. Preferably components which require data entry or access will include bar code scanners or other electronic entry devices.

Preferably, a plurality of central monitoring systems 14 are located throughout a facility as is seen in FIG. 1. Transfer of a patient from one central monitoring system 14 to another can be accomplished either by manually initiating a transfer function at the initiating central monitoring system 14, or can be accomplished automatically by sensing when a patient enters a zone of wireless monitoring coverage allocated to another central monitoring system 14. The manual transfer method has the advantage of requiring personnel to consciously execute the command and monitor the results of the transfer. In this way, no patient is inadvertently lost by the system. Appropriate confirmation can be provided to ensure the transfer has been effectively completed. In accordance with the automatic transfer method, the fields of the central monitoring system 14 preferably overlap so that continuous monitoring from a central location can take place.

Alternatively, monitoring can be switched from the central monitoring system 14 to the patient monitors 16 in transit. When a transfer is completed, the patient can be automatically registered into the appropriate central monitoring system 14 to which the patient is being transferred. Communication between the central monitoring systems 14 enable historical patient data to be transferred during or subsequent to the transfer procedure.

Figure 9:
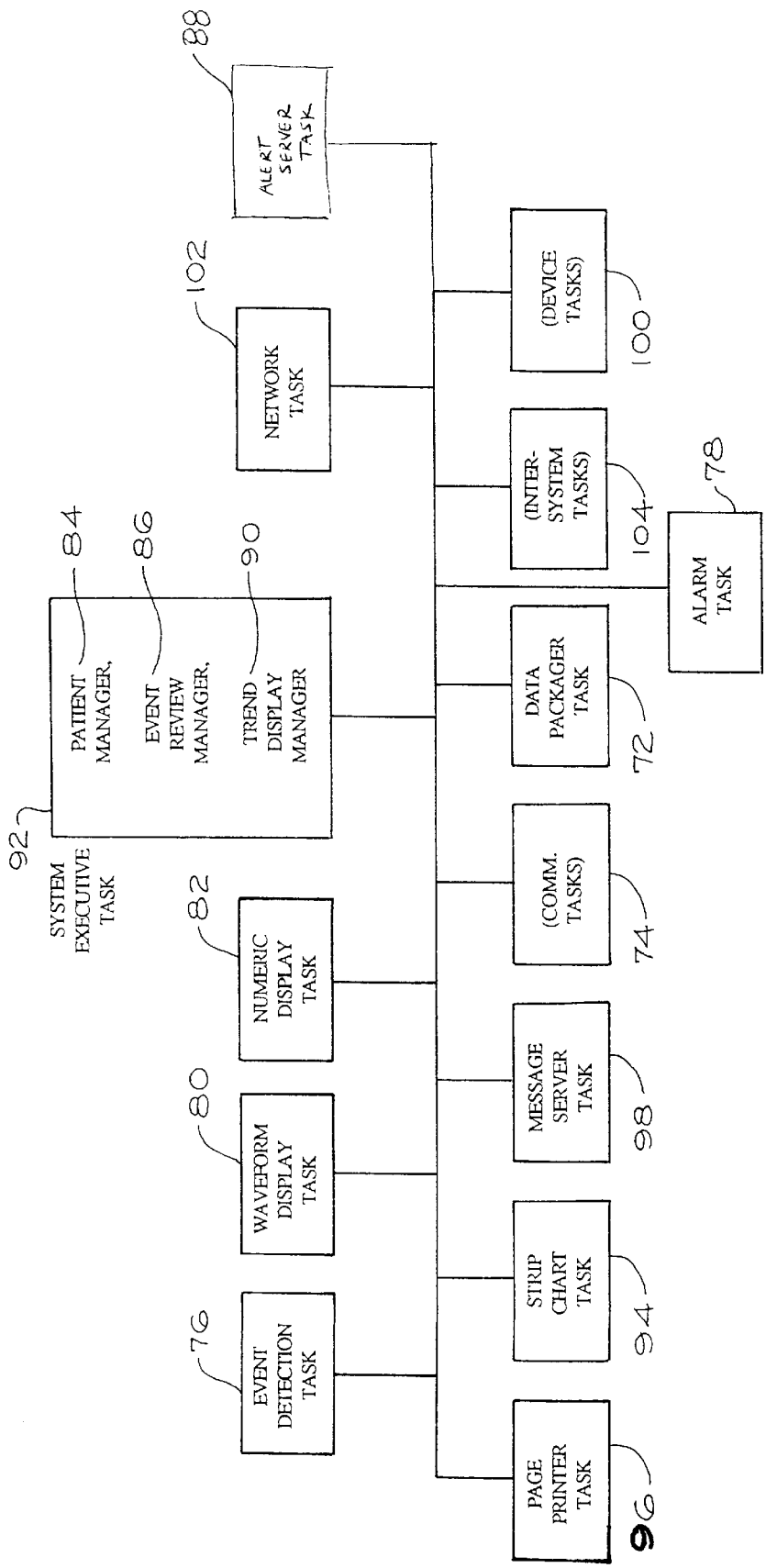
FIG. 9 is a block diagram illustrating software configurations and/or networks of one type which can be used in accordance with the central monitoring system of this invention.

Referring now to FIG. 9, an overview of the software system of the central monitoring system 14 of the preferred embodiment is shown. The software preferably incorporates a plurality of tasks operating under a real-time operating system. Incoming patient data such as therapy status data and vital sign data is collected by the Data Packager Task 72, which interprets the communications protocol and stores the waveforms and data into their respective memory buffers for further use. One or more Communications Tasks 74 manage the communications hardware in use (e.g., hardwired serial interface, network interface). The patient data is then reviewed for anomalous situations, including alarm limit violations, by the Event Detection Task 76. Audible and visual alarms are created by the Alarm Task 78. The display of waveforms and numeric vital signs are handled by the Waveform Display Task 80 and the Numeric Display Task 82, respectively. The process of automatically or manually admitting a patient to the central monitoring system 14, and maintaining demographic information, is controlled by the Patient Manager 84.

In one preferred embodiment, patient information is entered and stored based on an overall patient bar code system. In this embodiment, an electronic entry device 40, preferably a bar code scanner, is coupled to the central monitoring system 14, and patient admission data is controlled by the Patient Manager 84 based on the coded identification number assigned to a given patient and represented on their person as a bar code. The coded identification number is then employed to maintain a database of patient information, including information collected by the central monitoring system 14 as described below. In this way, patient admission data, electronic test results including waveforms, vital sign data, and events can be stored electronically in a single database.

The recording of alarm events, whether detected in the therapeutic device 12, the patient monitor 16 or the central monitoring system 14, takes place in the central monitoring system 14 through the Event Review Manager 86. Preferably, the event is a 36-second stored waveform chosen to bracket the time of the event. In this case, the central monitoring system preferably provides a display six seconds before the event, six seconds during the event, and for twenty-four seconds following the event. Other display sequences are possible. In preferred embodiments of this sort, the central monitoring system can analyze and store up to one hundred events per patient. Such events can be cataloged in an appropriate manner for easy retrieval, such as through an encoded bar code system as described above. Cataloged events can be used to provide a running total of events which can be reviewed and, as needed, compared to those events not yet reviewed. Events can also be reprinted, stored on a network or removable media archive, or deleted at any time according to standard operating procedure.

When the Event Review Manager 86 detects an alarm condition requiring immediate attention, or receives a signal from a patient monitor indicating such an event has occurred, a signal is forwarded to the Alert Server Task 88 as will be described more fully below.

Comprehensive trending of therapy status data such as infusion rate, total drug delivered, etc. and vital sign data such as heart rate, blood pressure, $SpO_2$, respiration rate, etc. over time is available through the Trend Display Manager 90. A 24-hour trending capability is preferred. The trending can involve single or multiple parameters including therapy status data, therapy delivery data, vital sign data and alert condition data. Activity information is also tracked through time. This is especially valuable in monitoring during rehabilitation therapy, where clinical data is collected during exercise activities. The Patient, Event, and Trend Managers together comprise the System Executive Task 92.

The printing of waveform and/or textual data is handled by the Strip Chart Task 94, if the printing is taking place on the chart recorder, or by the Page Printer Task 96, if taking place on a printer.

When a medical alert situation has been detected, a Message Server Task 98 processes requests for delivery of a message to a remote access device 42 made by the System Executive Task 92. The Message Server Task 98 maintains a list of information on messages which have been queued, including status (sent, acknowledged, canceled, etc.). This task also determines if a delivery has failed, and optimizes use of the memory reserved for message storage inside of the remote access device. If alert delivery fails, either because it could not be sent or was not acknowledged in a predetermined time period, the Message Server Task 98 can send an alarm to the central monitoring system 14 or alternatively, transmit the message to an alternative recipient. Any message to be sent to a remote access device 42, e.g., a medical alert message, is passed along to the appropriate Device Task (see below).

Because the Message Server Task 98 monitors a list of all messages sent in the system, it also performs the task of message memory maintenance for the remote access devices 42. Periodically, the Message Server Task 98 queries all known remote access devices 42 to determine if the message memory in some remote access device 42 is becoming full. If so, the Message Server Task 98 issues a command to the remote access device 42 to remove message(s) from its memory. The selection of messages is based upon age of the message, whether it has been read, and the priority of a medical alert (if any) associated with it. Furthermore, the Message Server Task 98 can delete data from the remote access device 42 which is no longer relevant, e.g., alerts which were responded to by other recipients and thus no longer need attention. A final advantage of this maintenance activity is that the central monitoring system 14 will know if a particular remote access device 42 is no longer available (e.g., battery low, has gone out of range, malfunctioning, etc.) by a lack of response to the maintenance query.

One or more Device Tasks 100 may be active in the system. Each type handles the details of communications with a particular type of remote access device (e.g., a pager versus a telephone or handheld computer). The Device Task 100 handles a request from a remote access device for information by accessing the patient, event, trend, and waveform data managed by the other tasks in order to format messages to be returned to the remote access device. In a preferred embodiment, the Device Tasks 100 may utilize the same wireless communications infrastructure as the Data Packager Task 72. This reduces overall systems cost, and permits tighter control of delivery time for medical alerts. This does not preclude the use of a variety of remote access devices 42. E.g., with IP (Internet Protocol) telephony, it is possible for a Device Task 100 to generate data in synthesized speech to telephonic remote access devices utilizing the same wireless infrastructure as a conventional pager.

The Network Task 102 comprises the means by which multiple central monitoring systems coordinate with each other over a network. The Inter-System Tasks 104, if active, support communications with various auxiliary systems 44, such as ECG diagnostic workstations or clinical information systems.

Figure 10:
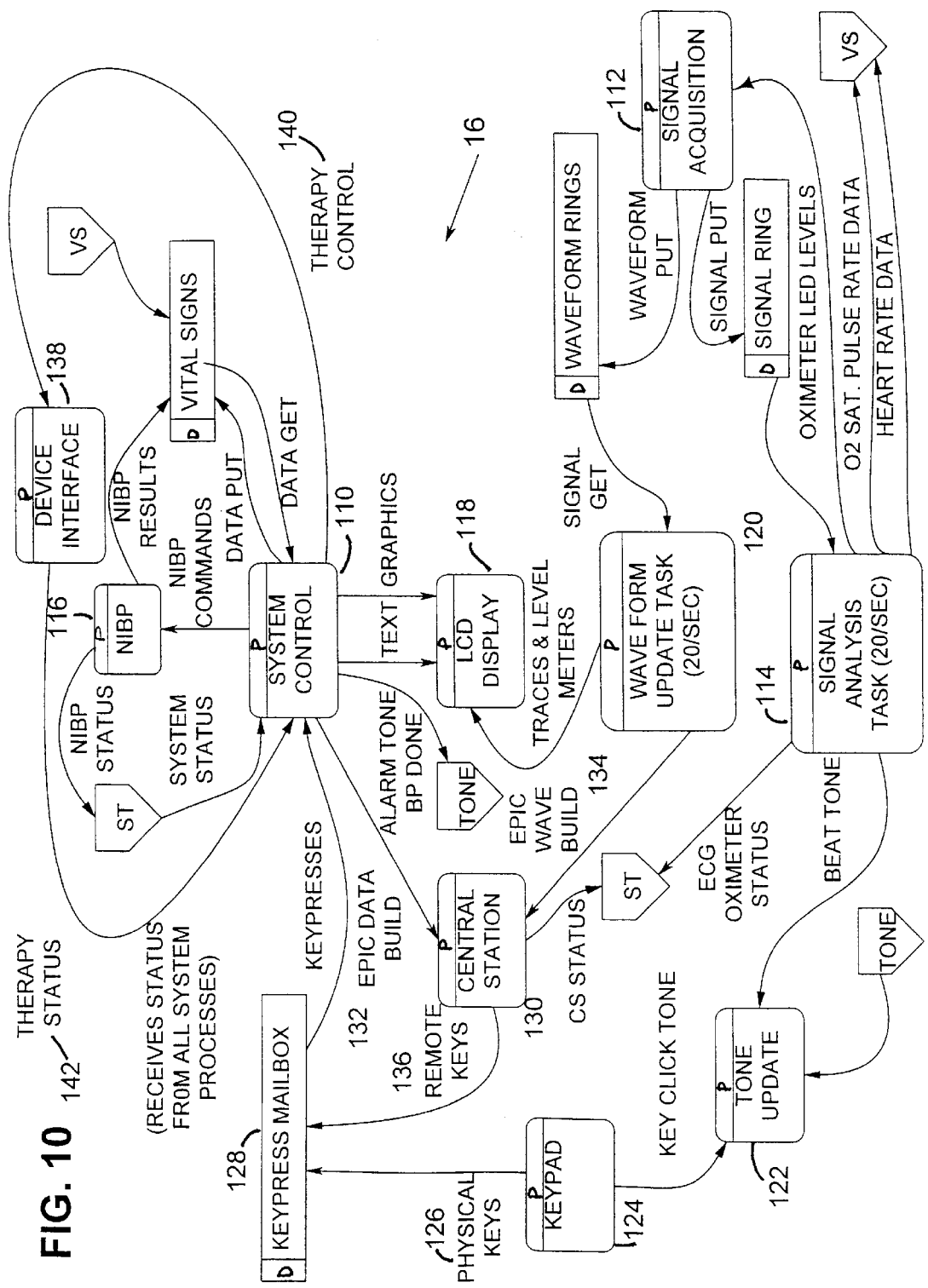
FIG. 10 is a block diagram showing a patient monitor constructed in accordance with one form of the invention.

Referring now to FIG. 10, a data flow diagram describing the operation of a patient monitor 16 is shown. The inclusion of both local and remote operation of the patient monitor 16 with bi-directional wireless communications on the patient monitor 16 poses a significant problem in local versus remote interaction. This problem is resolved in the software component of the monitor. Although the patient monitor 16 described below includes both vital sign monitoring and therapy status monitoring capabilities, it will be apparent to one of ordinary skill in the art that the patient monitor 16 can be constructed as a therapy status monitor, a vital sign monitor or both.

A System Control process 110 contains a body of software for coordinating processes in the patient monitor 16, providing common services, and managing shared resources. In the preferred embodiment, the System Control Process 110 includes a real-time operating system kernel, although other means of coordination such as "ladder logic" are available. The Signal Acquisition process 112, Signal Analysis Task 114, and NIBP process 116 are responsible for the conversion of analog signals from sensors in proximity to the patient's body into digital representation; processing of those signals including filtering and transformation; and interpretation of the processed signals to yield vital sign information. The local display is managed by the LCD Display process 118, receiving waveform data from the Wave Update Task 120 and textual data including numeric values from the System Control process 110. Audio tone generation is accomplished by the Tone Update process 122.

The local keypad input is handled by the Keypad process 124, which produces a series of messages labeled physical keys 126 sent to a Keypress mailbox 128. These messages are merely an ASCII representation of the key pressed; typically, one keypress is translated into one message to the mailbox, although the message representation allows a string of multiple keypresses. Other representations of the key pressed are possible, such as binary codes, bit masks, or software function addresses; these should all be considered within the spirit and scope of this invention. The Keypress mailbox 128 is periodically examined by the System Control process 110; any messages present are read, and the appropriate actions taken, including side-effects such as changing the content of menu items currently visible on the LCD display 118.

The Central Station process 120 is responsible for messages going to and from the central station 14 via the wireless communications. This includes transmission of EPIC data packets 132 for vital signs (heart rate, blood pressure, etc. and alert conditions such as ECG lead off) and therapeutic status (data such as IV pump flow rate and alert conditions such as low battery and bag empty) as well as EPIC wave packets 134 (ECG and plethysmograph waveforms). As part of its logic, the Central Station process 130 interprets commands received from the central monitoring system 14, and creates a series of messages to the Keypress mailbox 128 labeled remote keys 136 to execute the indicated commands. Such messages contain additional coding indicating the source of the keypresses was the central monitoring system 14.

The Device Interface process 138 manages the communications with a directly connected therapeutic device 12. Therapy Control 140 commands are sent from the System Control process 110 via the Device Interface 138 to initiate communications and request status in the therapeutic device 12. Optionally, this may also include commands to control the course of therapy delivered to the patient. Therapy Status 142, including numerical measurements as well as status and alarm information, is transferred back to the System Control process 110 from the therapeutic device 12 via the Device Interface process 138. The System Control process 110 may then interpret the information from the therapeutic device, store, display, and/or forward it to the central monitoring system via the Central Station process 130.

A mailbox such as the Keypad mailbox 128 operates as a FIFO (first-in, first-out) buffer; i.e., the mailbox maintains the temporal order of messages sent and removed from it. By translating a series of one or more commands received from the central station 14 into a single remote keys message 136, the Central Station process 130 can ensure that a sequence of operations requested remotely is completed without interruption by local interactions represented by physical keys messages 126. Furthermore, any desired side effects such as updating menu items visible upon the LCD display 118 will automatically take place. The System Control process 110, having available the fact that a keypress message originated remotely, can take further steps to reduce confusion of the local operator, including issuance of a warning tone, or inhibiting further local keypress processing for a period of time. The operations representing physical keys 126 and remote keys 136 are overlapping but not identical sets. Thus is it possible to prevent some local operations (e.g., zeroing an invasive pressure line) from being done remotely, and prevent some remote operations (e.g., switching a wireless communications channel selection) from being done locally. The same coordination methods apply for the remote control of therapeutic devices, and are particularly important due to the critical nature of therapeutic delivery. It should be apparent that other paradigms for representing a sequence of operations, such as a linked list of function calls, may also be useful for coordinating the local and remote operation, and fall within the spirit and scope of this invention.

Other parameters and waveforms that can be monitored include invasive pressures at multiple sites, respiration, body temperature, inspired and expired $CO_2$ levels in inspired and expired air, $O_2$ levels in inspired and expired air, anesthetic levels including nitrous oxide levels in inspired and expired air. It will be apparent to one of ordinary skill in the art that the patient monitors 16 can include any number of conventional monitoring devices for monitoring these parameters and waveforms.

Figure 11:
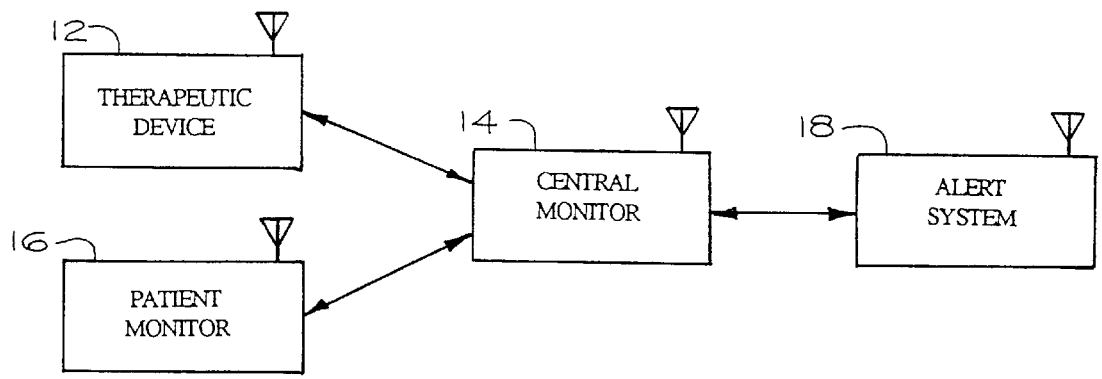
FIG. 11 is a block diagram of a medical monitoring and alert system constructed in accordance with another embodiment of the invention.
Figure 12:
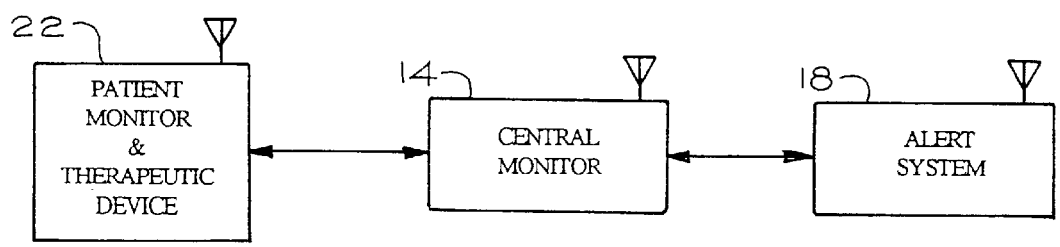
FIG. 12 is a block diagram of a medical monitoring and alert system constructed in accordance with a third embodiment of the invention.
Figure 13:
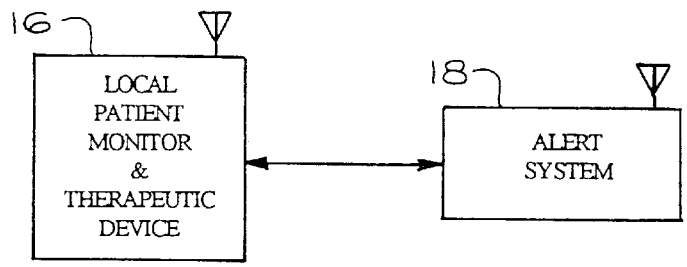
FIG. 13 is a block diagram of a medical monitoring and alert system constructed in accordance with a fourth embodiment of the invention.

Referring now to FIG. 11, an alternative embodiment of the invention is shown. Here, the patient monitor 16 and therapeutic device 12 each include a transceiver for communicating directly with the central monitoring system 14. In this embodiment, the network interface 20a in the therapeutic device 12 comprises a transceiver which communicates directly with the central monitoring system 14. The central monitoring system 14 and alert system 18 are as described above. Another alternative embodiment is shown in FIG. 12. Here, the patient monitor 16 and therapeutic device 12 are combined to form a single patient monitor/therapeutic device 22. The patient monitor/therapeutic device 22 performs all of the functions of the patient monitor and therapeutic device described above. All communications to the central monitoring system 14 are through a single transceiver. Yet another embodiment of the invention is shown in FIG. 13. Here, a plurality of combined patient monitor/therapeutic devices 16 are coupled to an alert system 18 through a wireless communications system.

While preferred embodiments have been illustrated and described, it should be understood that changes and modifications can be made thereto without departing from the invention in its broader aspects. Various features of the invention are defined in the following claims.

We claim:

1. A medical therapy delivery system comprising:
   a bi-directional communications network for digital data, the communications network including a hardwired communications segment and a wireless communications segment;
   at least one therapeutic device including a communications port, the therapeutic device adapted to control the delivery of therapy to a patient, and the therapeutic device transmitting therapy status data and alert condition data;
   at least one central monitoring system;
   at least one patient monitor for receiving therapy status data, the patient monitor linked to the at least one therapeutic device through said bi-directional communications network and linked to said at least one central monitoring system through the wireless communications segment of the communications network; and
   a remote access device linked to the at least one central monitoring system through the wireless communications segment, the remote access device providing at least patient therapy status data and alert condition data to a remote caregiver.

2. The medical therapy delivery system as defined in claim 1, wherein the therapeutic device comprises a fluid delivery system.

3. The medical therapy delivery system as defined in claim 2, wherein the therapy status data includes at least one of an infusion rate, a volume to be infused, and a volume infused.

4. The medical therapy delivery system as defined in claim 1, wherein the therapeutic device comprises a respiration delivery system.

5. The medical therapy delivery system as defined in claim 4, wherein the therapy status data includes at least one of a breath rate set, a breath rate actual, and an airway pressure.

6. The medical therapy delivery system as defined in claim 1, wherein the therapeutic device comprises a patient warming device.

7. The medical therapy delivery system as defined in claim 6, wherein the therapy status data includes at least one of an expected temperature and an actual temperature of a patient.

8. The medical therapy delivery system as defined in claim 1, wherein the therapeutic device is linked to the patient monitor through a hardwired serial link.

9. The medical therapy delivery system as defined in claim 1, wherein the therapeutic device is linked to the patient monitor through the wireless segment.

10. The medical therapy delivery system as defined in claim 1, wherein the therapeutic device is a hemodialysis machine.

11. A medical monitor and alert system for alerting medical personnel to the status of a patient, the system comprising:
    a bi-directional communications network for digital data, the communications network comprising a hardwired communications segment and a wireless communications segment, wherein the hardwired communications segment and the wireless communications segment each employ bi-directional communications;
    at least one therapeutic device adapted to control the delivery of therapy to a patient;
    at least one patient monitor for monitoring the physiological condition of the patient and for monitoring a therapy delivered to the patient, the patient monitor including a network interface for receiving therapy status data and alert condition data from at least one therapeutic device and for communicating therapy status data, physiological data, and alert condition data through the communications network;
    at least one central monitoring system including a network interface for receiving the therapy status data and alert condition data from the at least one patient monitor and for communicating therapy status data, physiological data, and alert condition data through the communications network; and
    an alert system comprising at least one remote access device linked to the communications network through the wireless communications segment of the communications network, the remote access device providing patient therapy status data and alert condition data to a remote caregiver along with patient physiological data, wherein the central monitoring system is adapted to transmit an alert signal when an alert condition is detected, and the remote access device is adapted to transmit a response signal to the central monitoring system when the alert signal is received.

12. The medical monitor and alert system as defined in claim 11, wherein the wireless bi-directional communications link employs frequency hopping spread spectrum RF communications in the ISM band.

13. The medical monitor and alert system as defined in claim 11, wherein the hardwired segment of the communications network is coupled to the wireless segment through at least one antenna coupled to the hardwired segment.

14. The medical monitor and alert system as defined in claim 11, wherein the hardwired communications link comprises a local area network.

15. The medical monitor and alert system as defined in claim 11, wherein the hardwired segment of the communications network comprises an ethernet backbone.

16. The medical monitor and alert system as defined in claim 11, wherein the communications network employs TCP/IP and UDP protocols to control communications between the therapeutic devices, the patient monitors, the central monitoring system, and the alert system.

17. The medical monitor and alert system as defined in claim 11, wherein the central monitoring system controls at least one physiological monitoring parameter at the patient monitor and controls at least one therapy delivery parameter at the therapeutic device.

18. A medical monitoring system comprising:
  a communications network for bi-directional communications, the communications network including a hardwired communications segment and a wireless communications segment, the hardwired communications segment being coupled to the wireless bi-directional communications link through at least one antenna;
  a plurality of therapeutic devices for controlling the delivery of therapy to patients;
  a plurality of patient monitors for monitoring physiological conditions of patients;
  a plurality of central monitoring systems for receiving therapy status and alert condition data from said therapeutic devices; and
  a plurality of remote access devices for providing patient physiological and therapy status data and alert condition data to remote caregivers;
  wherein each of the patient monitors, each of the central monitoring systems, and each of the remote access devices are identified by a unique identity code such that each of the plurality of patient monitors, the plurality of central monitoring systems and the remote access devices are adaptable to communicate with each of the remaining patient monitors, central monitoring systems, and remote access devices through the hardwired communications segment and the wireless communications segment.

19. The medical monitoring system as defined in claim 18, wherein the patient monitor monitors at least one therapy delivered to a patient and at least one physiological parameter of the patient.

20. The medical monitoring system as defined in claim 18, wherein each of the plurality of therapeutic devices are identified by a unique identity code such that each of the plurality of therapeutic devices is adaptable to communicate with each of the remaining patient monitors, central monitoring systems, and remote access devices through the communications network.

21. The medical monitoring system as defined in claim 18, further comprising at least one auxiliary system coupled to the communications network, wherein the auxiliary system is adapted to receive patient data from the central monitoring systems through the communications network.

22. The medical monitoring system as defined in claim 18, further comprising at least one electronic data entry device for entering caregiver, patient, medication, therapy, and device identification information.

23. The medical monitoring system as defined in claim 22, wherein the data entry device is a barcode scanner.

24. A method for monitoring a therapy delivered to an ambulatory or mobile patient, the method comprising the steps of:
  coupling to the patient, a therapeutic device adapted to control delivery of therapy to the patient and to transmit therapy status data;
  coupling the therapeutic device to at least one central monitoring system through a bi-directional communications network;
  coupling the central monitoring system to an alert system through the communications network;
  transmitting the therapy status data to the central monitoring system through the communications network;
  displaying the therapy status data at the central monitoring system;
  evaluating the therapy status data for an alert condition; and
  transmitting an alarm message to the alert system when the alarm condition is detected until a message received signal from the alert system is received by the central monitoring system.

25. The method as defined in claim 24, further comprising the step of periodically reviewing a memory component of the remote access device to determine an amount of free memory.

26. The method as defined in claim 24, further comprising the steps of determining when a message has been received at the remote access device and when a message has been opened at the remote access device.

27. The method as defined in claim 24, further comprising the step of assigning a primary recipient for a message to a first remote access device in the alert system and a secondary recipient for a message to a second remote access device in the alert system.

28. The method as defined in claim 24, further comprising the step of forwarding a message from a first remote access device in the alert system to a second remote access device when the first recipient cannot respond.

29. A medical monitor and alert system comprising:
  a bi-directional communications network including a hardwired communications segment and a wireless communications segment;
  at least one therapeutic delivery device adapted to control the delivery of therapy to a patient and to transmit therapy status data through a hardwired serial link;
  at least one patient monitor adapted to receive physiological parameter data pertaining to at least one physiological parameter of a patient and to receive transmitted therapy status data from the therapeutic delivery device through the hardwired serial link, the patient monitor further adapted to transmit the therapy status data and physiological parameter through the wireless communications segment of the communications network;
  at least one central monitoring system adapted to receive the therapy status data and physiological parameter data from the patient monitor and to transmit the therapy status data, physiological parameter data and alert condition data to an alert system through the wireless communications segment of the communications network; and
  an alert system comprising at least one remote access device providing patient therapy status data and alert condition data to a remote caregiver along with the patient physiological parameter data, the remote access device adapted to receive the therapy status data, physiological parameter data, and alert condition data from the central monitoring system through the wireless communications segment of the communications network, and to transmit an acknowledge signal to the central monitoring system when the data has been received.

30. The medical monitor and alert system as defined in claim 29, wherein the central monitoring system is linked to a second central monitoring system through a hardwired communications segment of the communications network.

31. The medical monitor and alert system as defined in claim 29, wherein the remote access device comprises at least one of a pager, a telephone, a portable computer, or a PDA.

32. The medical monitor and alert system as defined in claim 29, wherein the central monitoring system is further linked to a clinical information system through a hardwired communications segment of the communications network.

33. The medical monitor and alert system as defined in claim 11, wherein at least one patient monitor is linked to at least one therapeutic device through a device interface.

34. The medical monitor and alert system as defined in claim 11, wherein at least one patient monitor is linked to at least one therapeutic device through an RS-232 link.

* * * * *

UNITED STATES PATENT AND TRADEMARK OFFICE
CERTIFICATE OF CORRECTION

PATENT NO.   : 6,406,426 B1                                         Page 1 of 1
DATED        : June 18, 2002
INVENTOR(S)  : James L. Reuss and Michael J. Henry It is certified that error appears in the above-identified patent and that said Letters Patent is hereby corrected as shown below:

<u>Title page,</u>
Item [73], "Criticare Systems" should be -- Criticare Systems, Inc. --

Signed and Sealed this

Fourth Day of February, 2003

JAMES E. ROGAN
*Director of the United States Patent and Trademark Office*